United States Patent [19]

Ehman

[11] Patent Number: 5,977,770
[45] Date of Patent: Nov. 2, 1999

[54] MR IMAGING OF SYNCHRONOUS SPIN MOTION AND STRAIN WAVES

[75] Inventor: Richard L. Ehman, Rochester, Minn.

[73] Assignee: Mayo Foundation for MEdical Education and Research, Rochester, Minn.

[21] Appl. No.: 08/719,605

[22] Filed: Sep. 25, 1996

Related U.S. Application Data

[62] Division of application No. 08/325,834, Oct. 9, 1994, Pat. No. 5,592,085.

[51] Int. Cl.⁶ .................................................. G01V 3/00
[52] U.S. Cl. ............................................. 324/318; 600/421
[58] Field of Search .................................... 324/309, 307, 324/312, 315, 300, 318, 322; 600/421, 410

[56] References Cited

U.S. PATENT DOCUMENTS

| | | | |
|---|---|---|---|
| 4,543,959 | 10/1985 | Sepoponen | 324/309 |
| 5,131,392 | 7/1992 | Jolesz et al. | 324/309 |
| 5,284,144 | 2/1994 | Delannoy et al. | 324/315 |

*Primary Examiner*—Louis Arana
*Attorney, Agent, or Firm*—Quarles & Brady, LLP

[57] ABSTRACT

A scan using an NMR imaging system is carried out while applying an oscillating stress to the object being imaged. An alternating magnetic field gradient synchronized with the applied stress is employed in the NMR imaging pulse sequence to detect and measure synchronous spin motion throughout the field of view. The direction of the alternating gradient and/or the applied stress may be changed to measure and image the elastic properties of the object.

4 Claims, 10 Drawing Sheets

MR IMAGING OF SYNCHRONOUS SPIN MOTION AND STRAIN WAVES

This is a division of application Ser. No. 08/325,834 filed Oct. 19, 1994 now U.S. Pat. No. 5,592,085.

BACKGROUND OF THE INVENTION

The field of the invention is nuclear magnetic resonance imaging methods and systems. More particularly, the invention relates to the enhancement of MR image contrast.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant γ of the nucleus). Nuclei which exhibit this phenomena are referred to herein as "spins", and materials which contain such nuclei are referred to herein as "gyromagnetic".

When a substance such as human tissue is subjected to a uniform magnetic field (polarizing field $B_o$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment $M_t$, which is rotating, or spinning, in the xy plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which are superimposed on the polarizing field $B_o$, but which have a gradient along the respective x, y and z axes. By controlling the strength of these gradients during each NMR cycle, the spatial distribution of spin excitation can be controlled and the location of the resulting NMR signals can be identified.

It is well known that NMR can be used to detect and image the movement of spins. As disclosed in U.S. Pat. No. Re. 32,701 entitled "NMR Scanner With Motion Zeugmatography", acquired NMR signals can be sensitized to detect moving spins by applying a bipolar magnetic field gradient at the proper moment in each NMR measurement sequence. The phase of the resulting NMR signal measures the velocity of spins along the direction of the motion sensitizing magnetic field gradient. With more complex motion sensitizing magnetic field gradients, higher orders of motion, such as acceleration and jerk can also be measured with this method.

SUMMARY OF THE INVENTION

The present invention relates to the imaging of mechanical characteristics of an object, and more particularly, the production of an NMR image in which the intensity pattern reveals the mechanical properties of the object and in some applications, the pattern of propagation of mechanical strain waves within it. The invention includes the acquisition of NMR imaging data using an NMR pulse sequence in which a magnetic field gradient is alternated in polarity to phase encode moving spins, and a stimulus is applied to the object being imaged and is oscillated in magnitude in synchronism with the alternating magnetic field gradient. A phase image is reconstructed from the acquired NMR imaging data which depicts the synchronous movement of spins throughout the object resulting from the applied stimulus. Mechanical characteristics of the object are revealed by analysis of such images.

A general object of the invention is to produce an image which reveals the mechanical properties of an object. The applied stimulus may be a mechanical disturbance which sets up a traveling wave in the gyromagnetic medium that causes cyclic strain, or displacements of the spins. By synchronizing the alternating magnetic field gradient with the oscillatory applied stress, the movement of the spins in relation to the applied force is revealed by the phase of the acquired NMR signals. At locations where the spins move in phase with the applied stress the phase signal is maximum, at one polarity, and at locations where the spins oscillate out of phase with the applied stress the phase signals are maximum at the opposite polarity. These phase signals may be employed to modulate pixel intensity in a reconstructed image and the strain due to the applied stress throughout the imaged object is seen as a wave pattern. Changes in this wave pattern reveal the boundaries of regions of differing mechanical properties within the object.

Another object of the invention is to produce a series of images which reveal the strain wave propagation through an object. By synchronizing the application of the oscillating applied stress with the alternating magnetic field gradient at a series of different phase relationships, a corresponding series of phase images may be reconstructed showing the movement of the strain wave pattern through the object.

Yet another object of the invention is to produce an image which indicates the strain in an object produced by an applied force. A first phase image is produced with the oscillating stress applied, and a second phase image is produced without the oscillating stress applied. The difference between these two phase images is calculated and provides an image indicative of the strain in the object. These strain images provide a measure of a fundamental quantity of the medium in the form of displacement amplitude as a strain wave propagates through it. As a result, it becomes possible to calculate a number of fundamental mechanical properties pertaining to the viscoelastic nature of the gyromagnetic medium. They include, for example, velocity of propagation, Young's modulus and other moduli.

Another object of the invention is to produce images of the object indicative of its viscoelastic properties. By producing two phase images with the oscillating stress synchronized with the alternating magnetic field gradient at two different phase relationships, the wavelength of the propagated strain can be calculated at each image pixel. From this, the velocity of propagation can be calculated at each image pixel as well as Young's modulus.

Another object of the invention is to produce an image which indicates Poisson's ratio throughout the object. A first phase image is produced with the alternating gradient applied in the same direction as the oscillating stress, and a subsequent phase image is produced with the alternating gradient applied in an orthogonal direction. Poisson's ratio may be estimated at each pixel location from the resulting phase images. Since the velocity and wavelength of the propagated strain may also be measured, the viscous properties of the gyromagnetic medium can also be estimated. Using Young's modulus and Poisson's ratio, other moduli such as the shear modulus and the bulk modulus can be calculated and imaged.

Another general object of the invention is to produce an image of a patient which indicates the compliance of tissues. By acquiring a plurality of phase images of the patient with different arrangements of the oscillatory stress and the alternating magnetic field gradient, an image indicative of tissue compliance can be produced. This image provides the clinician with information comparable to that obtained by manually palpating the tissues.

Yet another object of the invention is to produce an NMR image in which contrast is enhanced for spins having oscillatory motion. By synchronizing the alternating magnetic field gradient with oscillatory movement of spins in the object being imaged, a phase image may be reconstructed in which the signals from the oscillatory spins are enhanced relative to stationary spins and randomly moving spins.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 1:
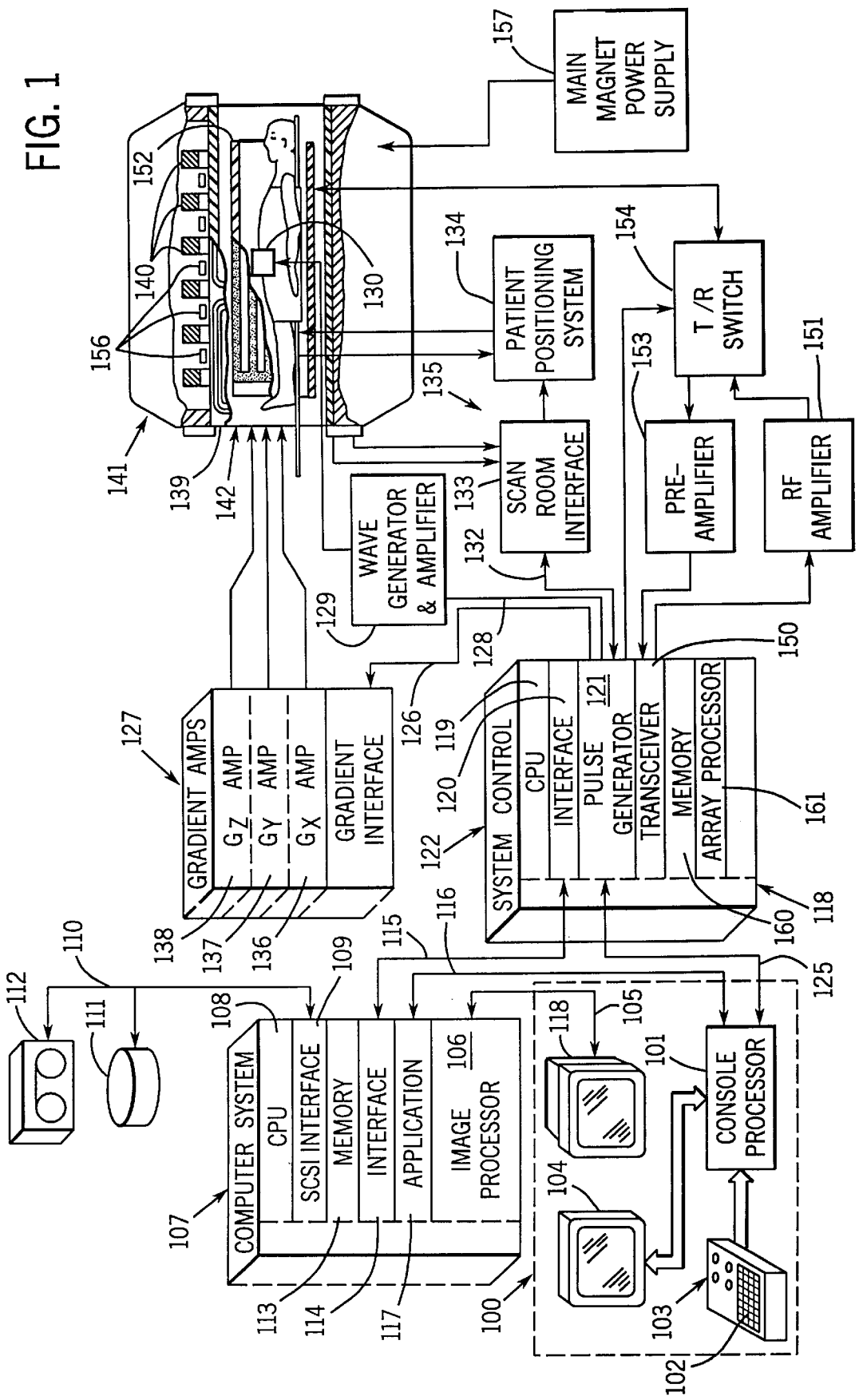
FIG. 1 is a block diagram of an NMR system which employs the present invention.

In general, the physical properties of tissue are measured by applying a stress (e.g. tension, pressure, or shear) and observing the resulting strain (e.g. elongation, compression, rotation). By measuring the resulting strain, elastic properties of the tissue such as Young's modulus, Poisson's ratio, the shear modulus, and the bulk modulus, can be calculated. By applying the stress in all three dimensions and measuring the resulting strain, the elastic properties of the tissue can be completely defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

The present invention provides a means for measuring the strain in gyromagnetic materials such as tissues using NMR methods and apparatus. The Larmor equation is given by $$\omega = \gamma \bar{B} \quad (1)$$

where X is the angular resonant frequency of the NMR signal produced by spins having a characteristic gyromagnetic ratio of γ when placed in a magnetic field having a density and direction $\bar{B}$. The magnetic field vector $\bar{B}$ can be broken down into two components $$\bar{B} = \bar{B}_o + r\bar{G}_r \quad (2)$$

where $B_o$ is the polarizing magnetic field, r is the location of the spins, and $G_r$ is the magnetic field gradient.

Since the angular frequency of the NMR signals produced by the spins is the rate of change of their phase, the phase of the spin signals as a function of time is as follows:

$$\phi(t) = \int \omega(t) dt. \quad (3)$$

Substituting equation (1), the relationship between NMR signal phase and the applied gradient field is obtained $$\phi(t) = \gamma \int G(t') r(t') dt', \quad (4)$$

where G and r are expressed as functions of time (t') for obtaining a general expression of the Larmor equation. This equation indicates that the NMR signal produced by moving spins will accrue a phase shift relative to that accrued by static spins when in the presence of a magnetic field gradient.

If an oscillating stress is applied to tissue along the direction r at an angular frequency $\omega_p$, a wave is launched and spins are displaced by amounts determined by the elastic properties of the tissue. If it is assumed that this propagation occurs without loss, the displacement (Δ) of spins at location (r) may be expressed as follows:

$$\Delta = \Delta_o \cos(\omega_p t + kr + \theta), \quad (5)$$

where $\Delta_o$ is the maximum displacement produced by the applied stress, k is the wave number, and θ is the phase offset of the spin displacement relative to the applied oscillating stress. The wave number k is equal to $2\pi$ radians divided by the wavelength (λ) of the propagated wave, and if it is assumed that the spin displacement occurs for just one cycle (t=0 to T) of the applied oscillating stress, then the NMR signal produced by the spin will accumulate a phase indicated by the following expression:

$$\phi(t) = \gamma \int_{t=0}^{t=\tau} G(t') \Delta_0 \cos(\omega_p t + kr + \theta) dt' \quad (6)$$

If the magnetic field gradient G(t') is constant during this time period, no phase signal will be accumulated. However, if the magnetic field gradient G(t') is synchronized with the applied stress and is switched in polarity half way through the time period (T), the phase of the NMR signal (φ) at the completion of the time period will be proportional to the displacement of the spins. This displacement along the r direction is the strain which results from the applied stress along the same direction r.

Figure 8:
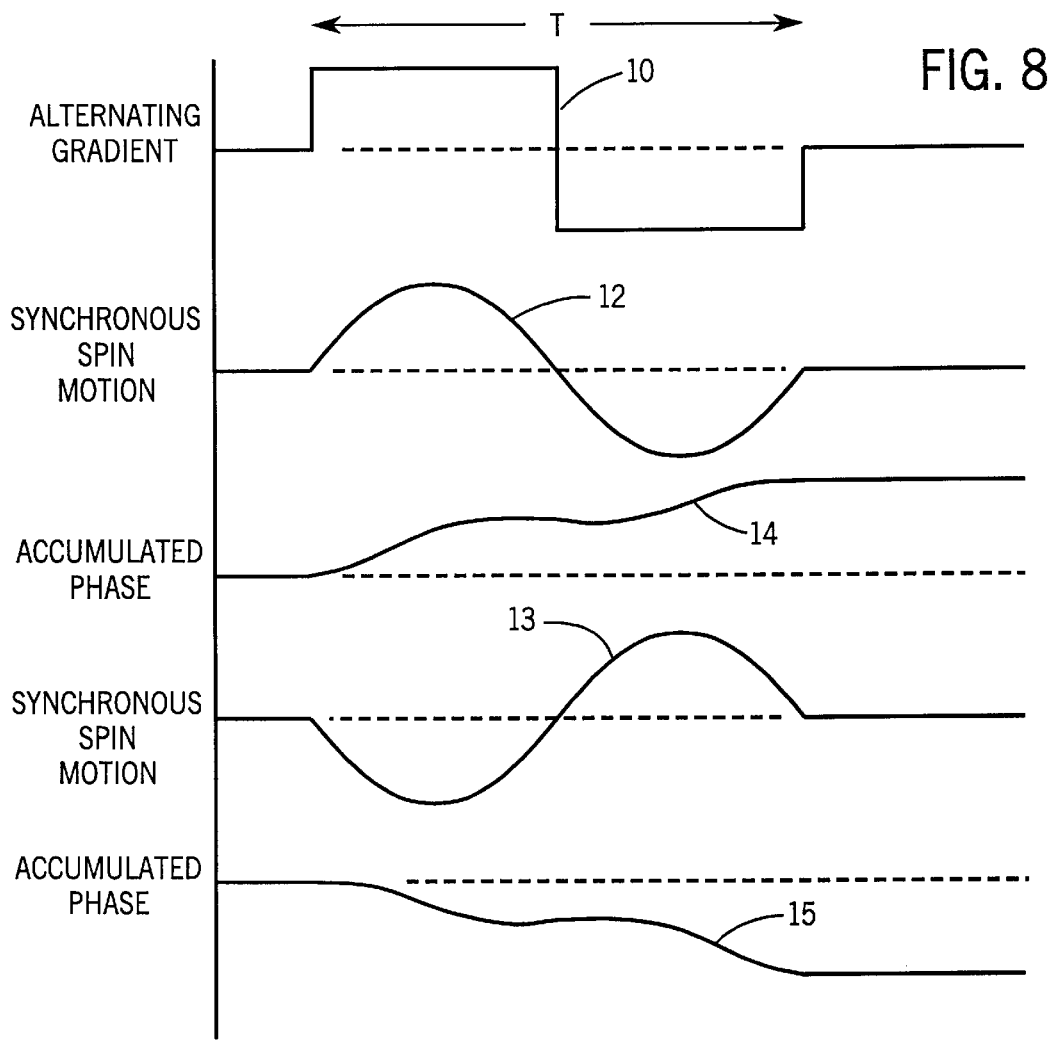
FIG. 8 is a graphic illustration of the phase accumulation in an NMR signal acquired with the pulse sequence of FIG. 3.
Figure 9:
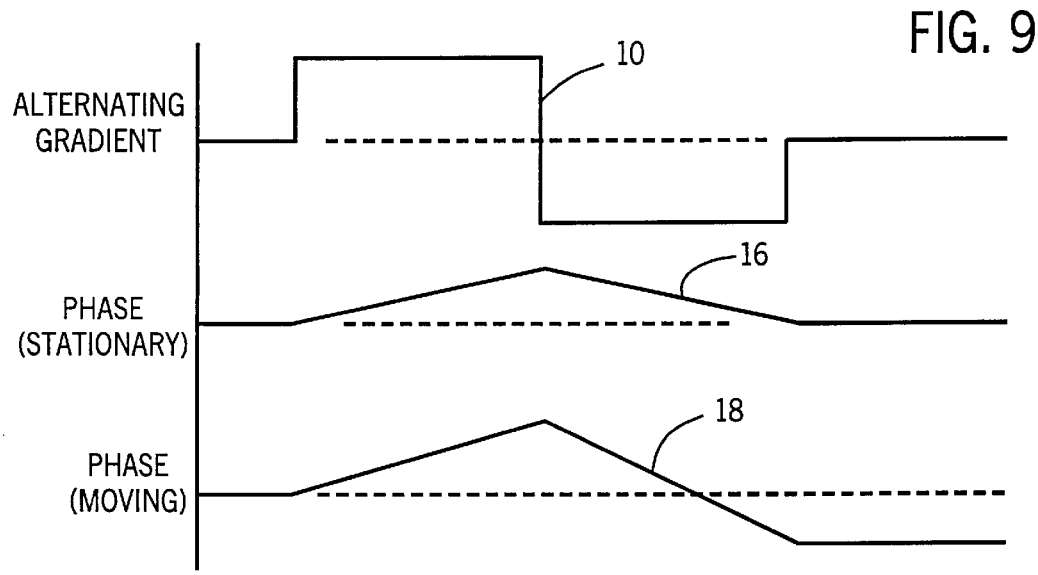
FIG. 9 is a graphic illustration of phase accumulation with the alternating gradient waveform reversed 180°.

The phase accumulation of the NMR signal due to spins in synchronous motion is illustrated in FIG. 8. An alternating magnetic field gradient that completes one bi-polar cycle during the time period T is indicated by waveform 10. Spins in synchronous motion and perfectly in phase with the alternating magnetic field gradient 10 is illustrated by the waveform 12, and the resulting accumulated phase in the NMR signal produced by these spins is indicated by the graph 14. On the other hand, synchronous spin motion 180° out of phase with the alternating gradient 10 is indicated by waveform 13 and the resulting phase accumulation is shown in graph 15. In contrast, FIG. 9 illustrates at graph 16 the phase of NMR signals produced by stationary spins, and graph 18 indicates the accumulated phase of constantly moving spins. At the completion of one cycle of the alternating gradient 10, the accumulated phase of stationary spins is nulled and the accumulated phase of constantly moving spins is proportional to their velocity along the direction of the gradient.

Because the displacements are very small, the gradient field G(t') is usually oscillated in synchronism with the applied stress for several cycles before the NMR signal is acquired. This enables the accumulated phase (') to reach a significant amount. A second NMR signal is then acquired with an identical pulse sequence, but without the application of the oscillatory stress. This second signal provides a reference phase ($\phi_R$) which may be subtracted from the accumulated phase $\phi_A$ to yield a value indicative of longitudinal strain ($S_L$).

These NMR measurements can be made, of course, with imaging gradients applied, and a strain image indicative of the longitudinal strain at each pixel may be reconstructed. This strain image has pixel values as follows:

$$S_L(t,r) = \Delta_o \cos(\omega_p t + kr). \quad (7)$$

If the measurement is repeated with the oscillating stress in the same direction, but with the alternating gradient G(t') oriented along each of the orthogonal axes, the displacements, along these axes can be determined and the orthogonal strain ($S_T$) calculated. From this information Poisson's ratio (σ) can be calculated as follows:

$$\sigma = S_T/S_L \quad (8)$$

Further information can be learned about the elastic properties of tissues by changing the phase relationship of the applied oscillatory stress and the synchronized alternating motion gradient. For example, if the phases are offset π/2 radians, a second strain image $S_o$ is produced having the following pixel values:

$$S_0(t, r) = \Delta_0 \cos(\omega_p t + kr + \pi/2) \quad (9)$$
$$= \Delta_0 \sin(\omega_p t + kr)$$

The gradient in each of the strain images $S_L$ and $S_o$ may be defined as follows:

$$\nabla S_L = \frac{\partial S_L}{\partial_x}\vec{i} + \frac{\partial S_L}{\partial_y}\vec{j} \quad (10)$$

$$\nabla S_0 = \frac{\partial S_0}{\partial_x}\vec{i} + \frac{\partial S_0}{\partial_y}\vec{j} \quad (11)$$

Using these gradients, the wave number (k) of the propagated wave at each image pixel can be calculated as follows:

$$k = \sqrt{|\nabla S_L| \cdot |\nabla S_L| + |\nabla S_0| \cdot |\nabla S_0|} \Big/ \sqrt{S_0^2 + S_L^2} \quad (12)$$

Knowing the frequency (f) of the applied oscillatory stress, the propagation velocity (c) can then be calculated at each image pixel as long as the viscosity effects are not significant.

$$\lambda = 2\pi/k$$

$$c = f\lambda \tag{13}$$

If the density ($\rho$) of the gyromagnetic medium is known, the propagation velocity (c) can be used to calculate Young's modulus (Y):

$$Y = c^2\rho. \tag{14}$$

Since compliance is the inverse of Young's modulus (i.e.1/Y), the compliance of the gyromagnetic medium may also be calculated. An image in which pixel intensity is determined by the calculated compliance has diagnostic value in medicine because such an image displays what a physician feels when manually palpating tissue. With the knowledge of Poisson's ratio ($\sigma$) and the Young's modulus (Y) all other values of moduli, namely the shear modulus ($\mu$) and the bulk modulus ($\beta$) may be calculated, since only two of these four elastic properties are actually independent. Bulk modulus ($\beta$) can be expressed from Young's modulus and Poissons ratio, in the following way:

$$Y = 3\beta(1-2\sigma). \tag{15}$$

Shear Modulus ($\mu$) can be expressed as follows:

$$Y = 2\mu(1+\sigma). \tag{16}$$

It should be apparent that the oscillatory stress may be applied in three orthogonal directions and the synchronized gradient field may also be applied in three separate orthogonal directions for each applied stress direction. Spin displacements ($\Delta, \eta, \Sigma$) in all three directions may be measured, and all the components of the strain dyadic (second-rank tensor field), given in the following matrix may be measured:

$$\begin{pmatrix} \frac{\partial \Delta}{\partial x} & \frac{\partial \eta}{\partial x} & \frac{\partial \Sigma}{\partial x} \\ \frac{\partial \Delta}{\partial y} & \frac{\partial \eta}{\partial y} & \frac{\partial \Sigma}{\partial y} \\ \frac{\partial \Delta}{\partial z} & \frac{\partial \eta}{\partial z} & \frac{\partial \Sigma}{\partial z} \end{pmatrix} \tag{17}$$

With these measurements it is possible to characterize all the elastic properties of the gyromagnetic medium under investigation using the above-described calculations.

DESCRIPTION OF THE PREFERRED EMBODIMENT

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 includes a number of modules which communicate with each other through a backplane. In addition to the application interface 117 and the image processor 106, these include a CPU module 108 that controls the backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan.

In the preferred embodiment of the invention the pulse generator module 121 also produces sync pulses through a serial link 128 to a wave generator and amplifier 129. The wave generator produces a sinusoidal voltage which is synchronized to the frequency and phase of the received sync pulses and this waveform is output though a 50 watt, dc coupled audio amplifier. A frequency in the range of 20 Hz to 1000 Hz is produced depending on the particular object being imaged, and it is applied to a transducer 130. The transducer 130 will be described in more detail below, and its structure depends on the particular anatomy being measured and imaged. In general, however, the transducer 130 produces a force, or pressure, which oscillates in phase with the sync pulses produced by the pulse generator module 121 and creates an oscillating stress in the gyromagnetic media (i.e. tissues) to which it is applied.

And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 141 which includes a polarizing magnet 140 that produces either a 0.5 or a 1.5 Tesla polarizing field that extends horizontally through a bore 142. The gradient coils 139 encircle the bore 142, and when energized, they generate magnetic fields in the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_o$, and the total magnetic field in the z direction is referred to as $B_z$, then $G_x=\partial B_z/\partial x$, $G_y=\partial B_z/\partial y$ and $G_z=\partial B_z/\partial z$, and the magnetic field at any point (x,y,z) in the bore of the magnet assembly 141 is given by $B(x,y,z)=B_o+G_x x+G_y y+G_z z$. The gradient magnetic fields are utilized to encode spatial information into the NMR signals emanating from the patient being scanned, and as will be described in detail below, they are employed to measure the microscopic movement of spins caused by the pressure produced by the transducer 130.

Located within the bore 142 is a circular cylindrical whole-body RF coil 152. This coil 152 produces a circularly polarized RF field in response to RF pulses provided by a transceiver module-150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil 152 are digitized by the transceiver module 150 and transferred to a memory module 160 which is also part of the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 as will be described in more detail below and conveyed to the operator console 100 and presented on the video display 118.

Figure 2:
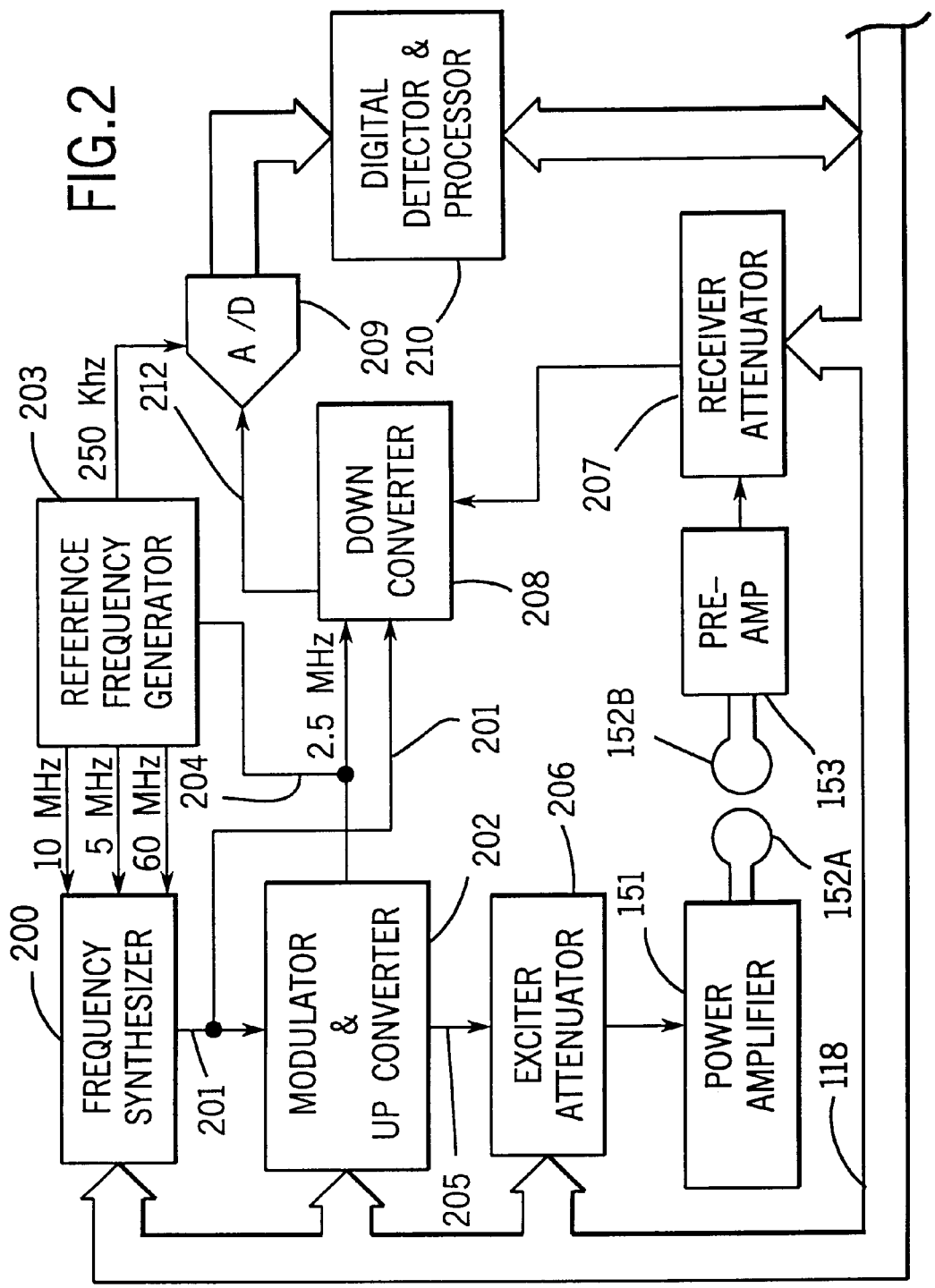
FIG. 2 is an electrical block diagram of the transceiver which forms part of the NMR system of FIG. 1.

Referring particularly to FIGS. 1 and 2, the transceiver 150 includes components which produce the RF excitation field $B_1$ through power amplifier 151 at a coil 152A and components which receive the resulting NMR signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the desired envelope. These stored digital values may, in turn, be changed from the operator console 100 to enable any desired RF pulse envelope to be produced. The modulator and up converter 202 produces an RF pulse at the desired Larmor frequency at an output 205.

The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the NMR signal produced by the subject is picked up by the receiver coil 152B and applied through the preamplifier 153 to the input of a receiver attenuator 207. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation.

The received NMR signal is at or around the Larmor frequency, which in the preferred embodiment is around 63.86 MHz for 1.5 Tesla and 21.28 MHz for 0.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20

MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Figure 3:
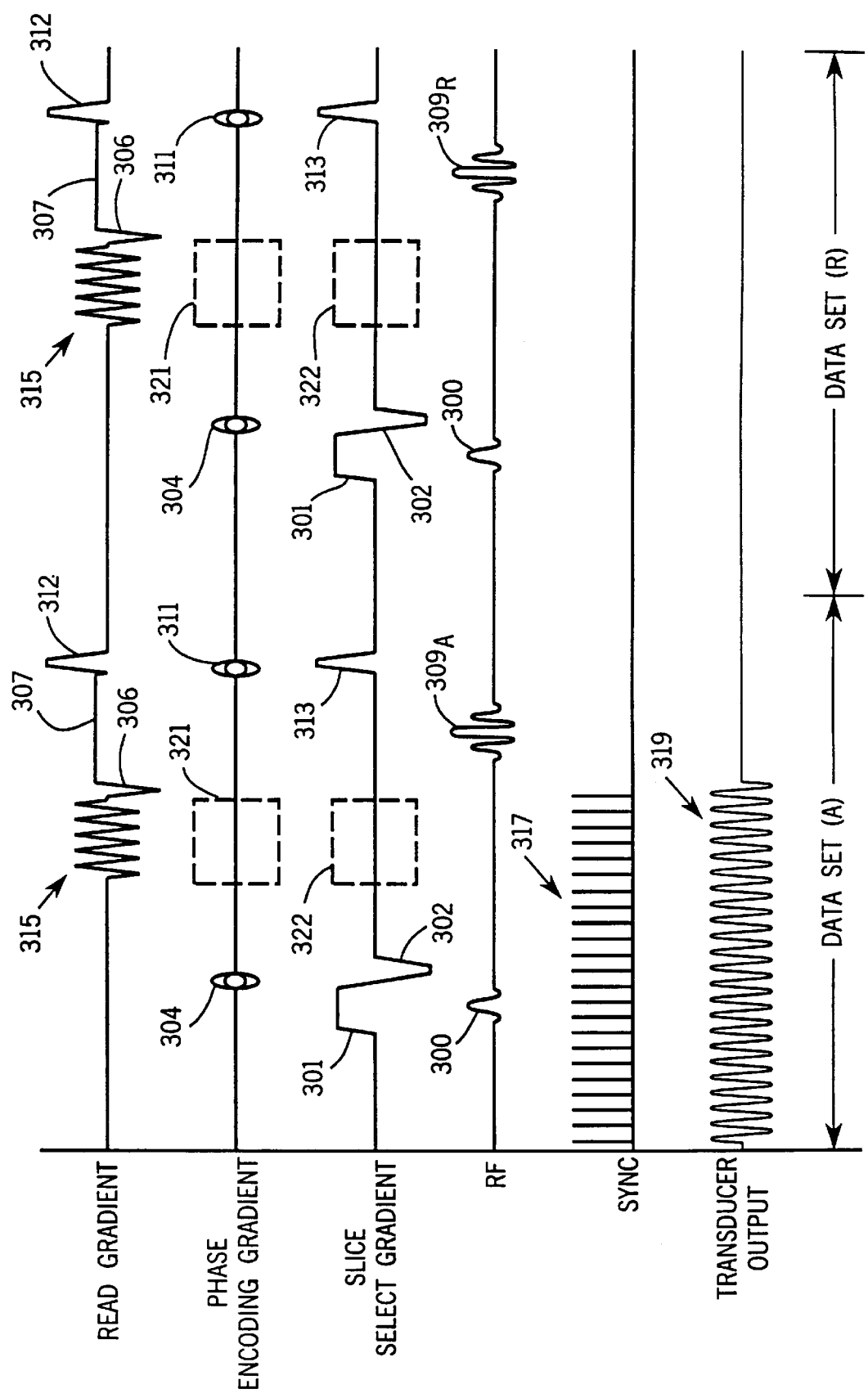
FIG. 3 is a graphic representation of a pulse sequence performed by the NMR system of FIG. 1 to practice the preferred embodiment of the invention.

Referring particularly to FIG. 3, a preferred embodiment of a pulse sequence which may be used to acquire NMR data according to the present invention is shown. Actually, two pulse sequences are shown, with the first being used to acquire NMR data for a synchronous spin motion image (A), and the second being used to acquire NMR data for a reference image (R). In the preferred embodiment, these two pulse sequences are alternated throughout the scan such that the corresponding views (i.e. phase encodings) in the data sets (A) and (R) are acquired at substantially the same moment in time.

The pulse sequences are fundamentally a 2DFT pulse sequence using a gradient recalled echo. Transverse magnetization is produced by a selective 90° rf excitation pulse 300 which is produced in the presence of a slice select gradient ($G_z$) pulse 301 and followed by a rephasing gradient pulse 302. A phase encoding gradient ($G_y$) pulse 304 is then applied at an amplitude and polarity determined by the view number of the acquisition. A read gradient ($G_x$) is applied as a negative dephasing lobe 306, followed by a positive readout gradient pulse 307. An NMR echo signal 309 is acquired 40 msecs. after the rf excitation pulse 300 during the readout pulse 307 to frequency encode the 256 digitized samples. The pulse sequence is concluded with spoiler gradient pulses 312 and 313 along read and slice select axes, and a rephasing gradient pulse 311 is applied along the phase encoding axis ($G_y$). As is well known in the art, this rephasing pulse 311 has the same size and shape, but opposite polarity of the phase encoding pulse 304. The pair of pulse sequences are repeated 128 times with the phase encoding pulse 304 stepped through its successive values to acquire a 128 by 256 array of complex NMR signal samples that comprise the data set (A) and a 128 by 256 array of complex NMR signal samples that comprise the reference data set (R).

To practice the present invention an alternating magnetic field gradient is applied after the transverse magnetization is produced and before the NMR signal is acquired. In the preferred embodiment illustrated in FIG. 3, the read gradient ($G_x$) is used for this function and is alternated in polarity to produce five bipolar, gradient waveforms 315. The alternating gradient 315 has a frequency of 200 Hz and a duration of 25 msecs. At the same time, the pulse generator module 121 produces sync pulses as shown at 317, which are also at a frequency of 200 Hz and have a specific phase relationship with the alternating gradient pulses 315. As explained above, these sync pulses 317 activate the transducer 130 to apply an oscillating stress 319 to the patient which has the same frequency and phase relationship. To insure that the resulting waves have time to propagate throughout the field of view, the sync pulses 317 may be turned on well before the pulse sequence begins, as shown in FIG. 3.

The phase of the NMR signal $309_A$ acquired during the first pulse sequence (A) is indicative of the movement of the spins. If the spins are stationary, the phase of the NMR signal is not altered by the alternating gradient pulses 315, whereas spins moving along the read gradient axis (x) will accumulate a phase proportional to their velocity. Spins which move in synchronism and in phase with the alternating magnetic field gradient 215 will accumulate maximum phase of one polarity, and those which move in synchronism, but 180° out of phase with the alternating magnetic field gradient 215 will accumulate maximum phase of the opposite polarity. The phase of the acquired NMR signal $309_A$ is thus affected by system phase errors and random movement of spins along the x-axis, as well as the "synchronous" movement of spins along the x-axis.

The reference pulse sequence is designed to measure the signal phase produced by sources other than synchronized spin movement. This is accomplished by repeating the identical pulse sequence, but without applying the oscillating stress 319. As a result, the phase of the acquired NMR signal $309_R$ will be affected by "static" system phase errors caused by field inhomogeneities and the like as well as the phase due to random spin movement along the x-axis. However, there will not be a phase component due to synchronous spin movement and the reference phase $\phi_R$ can, therefore, be subtracted from the phase $\phi A$ to yield the phase ($\phi$) due solely to synchronous spin motion.

The pulse sequence in FIG. 3 can be modified to measure synchronous spin movement along the other gradient axes (y and z). For example, the alternating magnetic field gradient pulses may be applied along the phase encoding axis (y) as indicated by dashed lines 321, or they may be applied along the slice select axis (z) as indicated by dashed lines 322. Indeed, they may be applied simultaneously to two or three of the gradient field directions to "read" synchronous spin movements along any desired direction.

The present invention may be implemented using most types of MR imaging pulse sequences. Gradient echo sequences can be readily modified to incorporate the alternating gradient as illustrated in the preferred embodiment. In some cases, however, the characteristics of a gradient echo sequence may not be ideal for a particular application of the technique. For example, some tissues (such as those with many interfaces between materials with dissimilar magnetic susceptibilities) may have a relatively short T2* relaxation time and therefore may not provide enough signal to obtain a noise-free image at the required echo delay time. In this setting, a spin echo implementation of the invention may be ideal, because for a given echo delay time TE, this pulse sequence is much less sensitive to susceptibility effects than a gradient echo sequence. When a spin echo pulse sequence is used, the alternating magnetic field gradient can be applied either before and/or after the 180° rf inversion pulse. However, if the alternating gradient is applied both before and after the rf inversion pulse, the phase of the alternating magnetic field gradient must be inverted 180° after the rf inversion pulse in order to properly accumulate phase.

In other applications, reduced acquisition time may be desirable. Fast spin echo and RARE sequences are rapid MRI sequences that acquire multiple views per TR cycle by applying different phase encoding gradients to each echo in a spin echo train. If 16 echoes, for instance, are acquired in each repetition of the sequence, then the total acquisition time for a complete image will be reduced by a factor of 16. One approach for modifying a fast spin echo sequence to implement the present invention is to insert the alternating gradient pulses between the initial 90° RF pulse and the first 1800 RF refocussing pulse, followed by a similar but inverted set of gradient pulses. The first echo in the train might be at a TE of 40–60 msec, but the spacing between subsequent echoes could be as short as 12–15 msec.

Echo-planar imaging ("EPI") is another approach for high speed MR acquisition. In one version of this technique, the spin echo created by standard 90° and 180° RF pulses is broken up into a series of 64–128 short gradient echoes by rapidly reversing the readout gradient. A different phase encoding is applied to each of the gradient echoes and therefore the acquired data from one shot of the sequence can, in principle, be used to reconstruct a complete image. One approach for modifying such an echo-planar sequence to implement the present invention is to insert alternating gradient pulses between the initial 90° RF pulse and the 180° RF refocussing pulse, followed by a similar but inverted set of alternating gradient pulses. Such a sequence permits phase images to be obtained in only a few seconds or less.

The number of cycles of the alternating magnetic field gradient used in each pulse sequence depends on the strength of the applied gradient field, the frequency of the synchronous movement to be measured, and the TE time of the pulse sequence. The phase sensitivity of the pulse sequence to synchronous spin movement is proportional to the integrated product of alternating gradient field amplitude and the displacement over time. The sensitivity may be increased by increasing the amplitude of the gradient field pulses and by increasing the area under each pulse by making them as "square" as possible. The duration of each gradient pulse is limited by the desired synchronous frequency, and hence more cycles of the alternating gradient waveform are required at higher frequencies to produce the same sensitivity as a lower frequency alternating gradient of the same amplitude and wave shape.

Phase sensitivity to synchronous motion can also be increased by applying both the alternating gradient pulses 315 and the sync pulses 317 during the reference pulse sequence. However, when this is done the phase of the alternating magnetic field gradient 315 must be inverted 180° relative to the sync pulses 317 so that the sign of the accumulated phase is reversed. In addition, the magnetic field gradients should be flow compensated as described, for example, in U.S. Pat. No. 4,728,890 by Pattany et al., which is hereby incorporated by reference. Such flow compensation removes any phase component due to random spin motion without significantly affecting the sensitivity to synchronous spin motion. Consequently, when the phase difference image is produced the phase accumulations due to synchronous spin motion add together, while phase accumulations due to other sources subtract and are thereby nulled.

If the synchronous frequency to be measured exceeds the frequency at which the magnetic field gradient can be switched, a lower harmonic frequency may be used for the alternating gradient. As long as the time period of one cycle of the alternating gradient corresponds with an odd number of cycles of the synchronous spin motion, the phase of synchronous spin motion will accumulate. For example, the alternating gradient frequency may be ⅓, ⅕, ⅐, ⅑, etc. of the synchronous motion frequency.

Figure 10A:
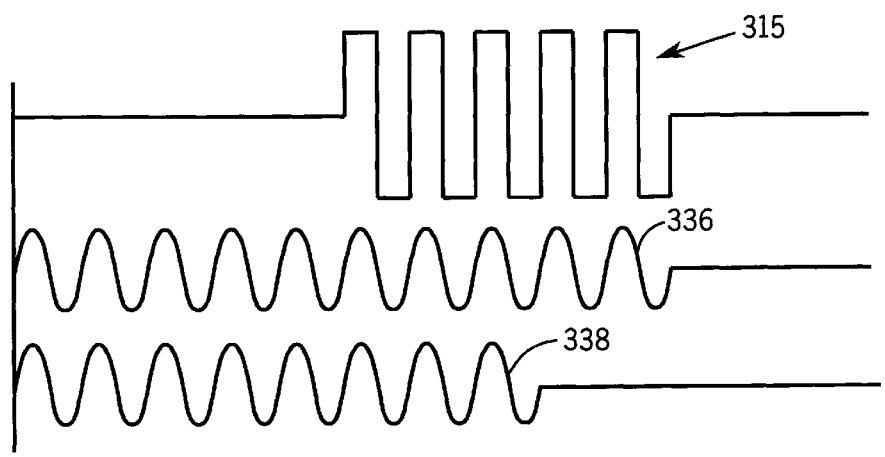
FIGS. 10a and 10b are graphic illustrations of alternative methods for applying the oscillating stress relative to the alternating gradient waveform in the pulse sequence of FIG. 3.

The oscillating stress may be applied by the transducer 130 in a number of ways. By starting the sync pulses 317 well before the alternating magnetic field gradient 315 as shown in FIG. 3, the synchronous spin motion propagates throughout the field of view of the reconstructed image. This will image the steady-state conditions in the medium when the oscillating stress is applied. If the sync pulses 317 are turned off just before the alternating gradient 315 is applied, spins adjacent to the transducer 130 are moving with less amplitude or not at all during the phase accumulation time period. This may be desired, for example, when regions deep beneath the surface are of primary interest and large strain effects in the image near the transducer 130 can be suppressed. This is shown, for example, in FIG. 10a where the synchronous stress variations are depicted by the waveforms 336 and 338. The stress oscillations may be terminated one cycle short, as shown by waveform 336 when phase accumulation near the transducer 130 is to be reduced only slightly, or it may be terminated sooner as shown by waveform 338 if more phase accumulation is to be prevented.

Figure 10B:
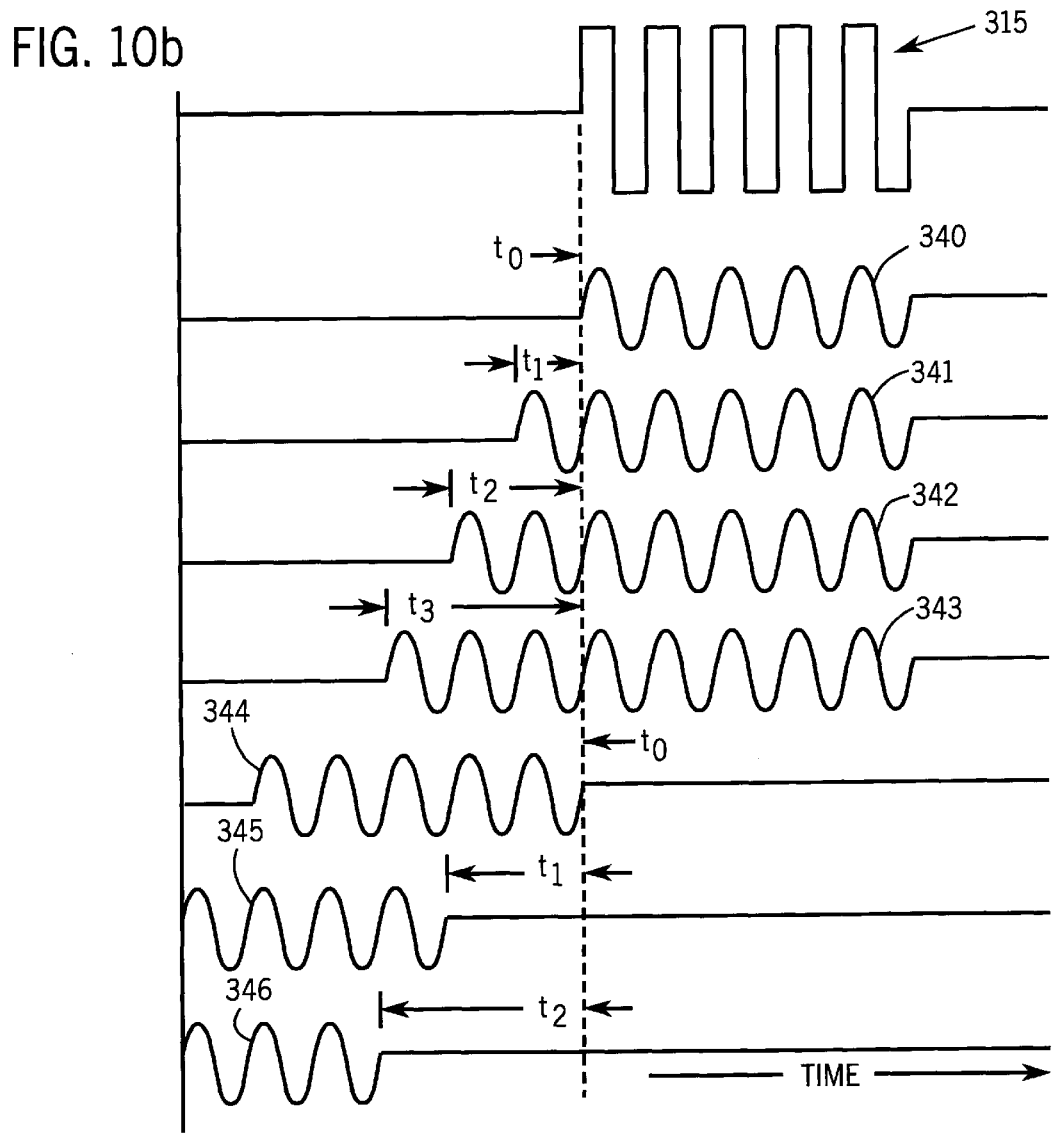

Referring particularly to FIG. 10b, the synchronous stress variations may only be applied for a moment in order to observe the mechanical impulse response or transient response of the gyromagnetic material. As indicated by waveforms 340–343, the burst of stress oscillations may be applied at different times ($t_0$, $t_1$, $t_2$, $t_3$, etc.) before the application of the alternating magnetic field gradient pulses 315 and a two-dimensional strain image reconstructed at each timing. A three-dimensional data set is thus acquired in which one of the dimensions is the time at which the stress oscillations are applied. The response of the spins at any image pixel location in the field of view can then be plotted as a function of time. The same procedure may be used to measure the response of the medium when the oscillating stress is turned off, as shown by the waveforms 344–346 in FIG. 10b.

In the preferred embodiment the frequency of the sync pulses 317 and the alternating magnetic field gradient 315 are constant during each scan. Other information can be acquired, however, if the frequency of either is varied. For example, if the frequency of the alternating gradient 315 is swept through a series of frequencies during each pulse sequence, or a series of acquisitions of each view are acquired at different alternating gradient frequencies, the mechanical response of the gyromagnetic material to a band of stress frequencies can be measured. Similarly, the sync pulses 317 can be swept through a series of frequencies during each pulse sequence or during a series of acquisitions of the same view to produce a band of synchronous spin movement frequencies. The same result may also be achieved by changing the shape of the applied oscillatory stress from substantially sinusoidal as depicted in FIG. 3 to some other shape such as a square wave, which contains higher frequency harmonics.

Such multi-frequency excitations and detections may be required in some applications where reflections cause standing waves. One such application, for example, is imaging the head where standing waves are formed by reflections off the skull. By imaging with multiple frequencies and adding or averaging the resulting signals, the effects of such standing waves can be reduced.

A scan using the pulse sequence of FIG. 3 is carried out under the direction of a program executed by the NMR system of FIG. 1. Since many different mechanical properties can be imaged according to the present invention, many different programs may be stored and called up for use by the operator. Some of these programs are illustrated in the drawings by flow charts and described in detail below. However, it can be appreciated that many variations from these specific examples are possible.

Figure 4:
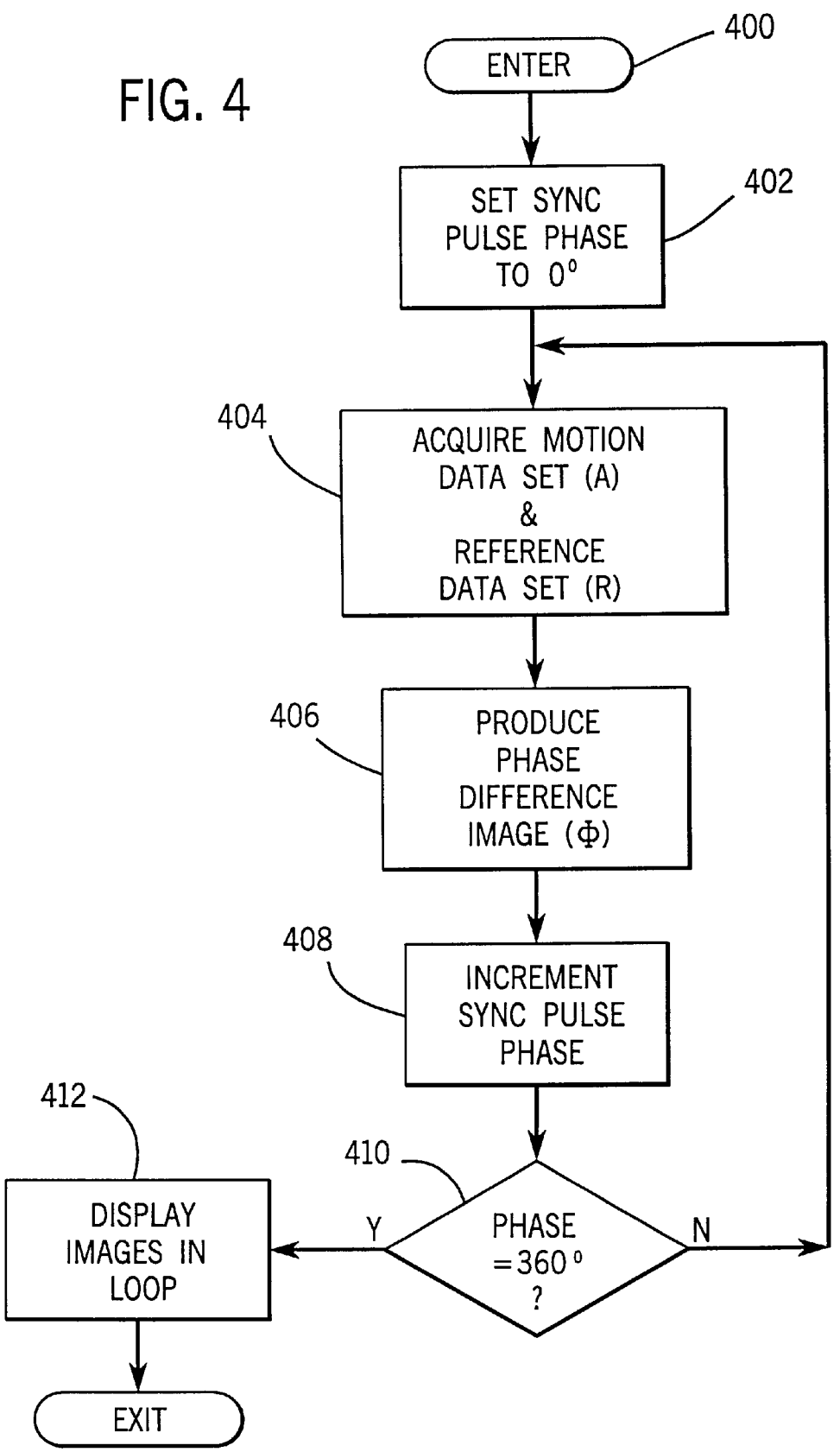
FIG. 4 is a flow chart which illustrates how the NMR system of FIG. 1 reconstructs a series of strain images in accordance with a first preferred embodiment of the invention using NMR data acquired with the pulse sequence of FIG. 3.

Referring particularly to FIG. 4, a scan may be performed according to the present invention to acquire NMR data from which ten images are reconstructed showing the propagation of strain through the gyromagnetic medium. The program for this scan is entered at 400 and the pulse sequence of FIG. 3 is downloaded to the pulse generator module 121. The sync pulses 217 in this pulse sequence are timed to be in phase with the alternating motion encoding gradient 215 as indicated at process block 402. The pulse sequence is then performed the necessary number of times to acquire two complete NMR data sets as indicated at process block 404. As described above, one of these data sets (A) is phase encoded with the transducer 130 energized, and the other data set (R) is a reference that is acquired with the transducer 130 de-energized. As will be described in detail below with reference to FIGS. 6a–6c, a single phase image (φ) is then reconstructed from these two NMR data sets (A) and (R) as indicated at process block 406. The intensity of each pixel in this phase image (φ) is determined by the phase imparted to spins moving in synchronism with the applied oscillatory stress. This synchronous movement is a measure of the strain in the gyromagnetic material and the phase image (φ) is, therefore, an image which shows by the brightness of its pixels the strain at corresponding locations (i.e. voxels) in the image plane.

This phase image is a snapshot of the strain at one moment in the applied stress cycle, and to see the strain at other moments, the phase relationship of the sync pulses 217 is changed, as indicated at process block 408, and the acquisition and image reconstruction process is repeated. The scan continues to acquire NMR data and reconstruct strain images at successive increments (for example, 36°) of sync pulse phase. When an entire 360° cycle has been captured in successive strain images, the system branches at decision block 410. The set of strain images may then be viewed consecutively to "animate" the propagation of strain through the gyromagnetic medium as indicated at process block 412.

The single or "animated" strain images obtained by this technique provide a view of the propagation of strain waves through the tissues imaged. Even without further processing, it is possible to qualitatively characterize tissue and to detect abnormalities by noting various features of the depicted waves such as wave-spacing, spatial phase, diffraction, and attenuation. The animated images are particularly useful for detecting small lesions such as tumors that differ in compliance from surrounding tissues, because the localized phase shift is more easily identified than in a single static strain image. A simple approach for integrating the information provided by these strain images with conventional modulus (anatomy) images provided by the same pulse sequence, is to multiply the corresponding gray scale values of the two types of images, thereby obtaining a composite image which provides both types of information.

Although the primary focus of most medical applications of the invented imaging technique is to characterize tissue and to detect focal abnormalities such as tumors, the technique is also useful for characterizing acoustic systems per se. For instance, the technique may be used to characterize an array of acoustic energy sources that are intended for tissue ablation or lithotripsy. By exciting each acoustic driver individually and obtaining a strain image according to the present invention, the precise strain pattern associated with each transducer can be shown in situ, thereby showing the effects of diffraction and phase shifts caused by intervening tissue. These strain images could then be used to determine the proper phasing pattern to be applied to each of the elements in the acoustic drive array, so as to yield maximum strain at the target within the patient. As a final check, the tailored excitation so-produced could be applied to all of the drivers in the array at a low power level and a strain image could be obtained to confirm that the acoustic strain is maximized at the target tissue. The strain image could also be used to exclude the possibility of collateral damage to other locations when therapeutic power levels are applied to the acoustic drivers.

While it is apparent that there are many medical applications of the invented imaging technique, it is also clear that the strain images provided by the technique are useful for a variety of industrial design and testing applications. For instance, it is a common requirement to assess the vibrational characteristics and stability of complex engine parts. Because it has not been possible to readily measure the internal strain caused by vibrational loading on such parts, it is often necessary to simulate such parameters using finite element analysis. The invented imaging method could be used to directly observe these phenomena. In this application, a model of the part would be made from a porous material that has a scaled approximation of mechanical properties of the real part. The pores of the model part would then be impregnated with a material such as oil, or water that would provide an MRI signal. Vibrational loading could then be applied, and the internal pattern of strain could be imaged using the invented method. As in medical applications, the objectives of non-medical applications include (1) characterization of material properties, (2) detection of focal flaws or abnormalities, (3) depicting the pattern of propagating waves in a transmitting medium, (4) characterizing an acoustical driver or array of drivers.

While strain images provide valuable information concerning the mechanical properties of the gyromagnetic media, the present invention enables one to measure and image many other mechanical properties as well. A scan which acquires the data necessary for such measurements may be carried out under the direction of a program illustrated by the flow chart in FIG. 5.

Figure 5:
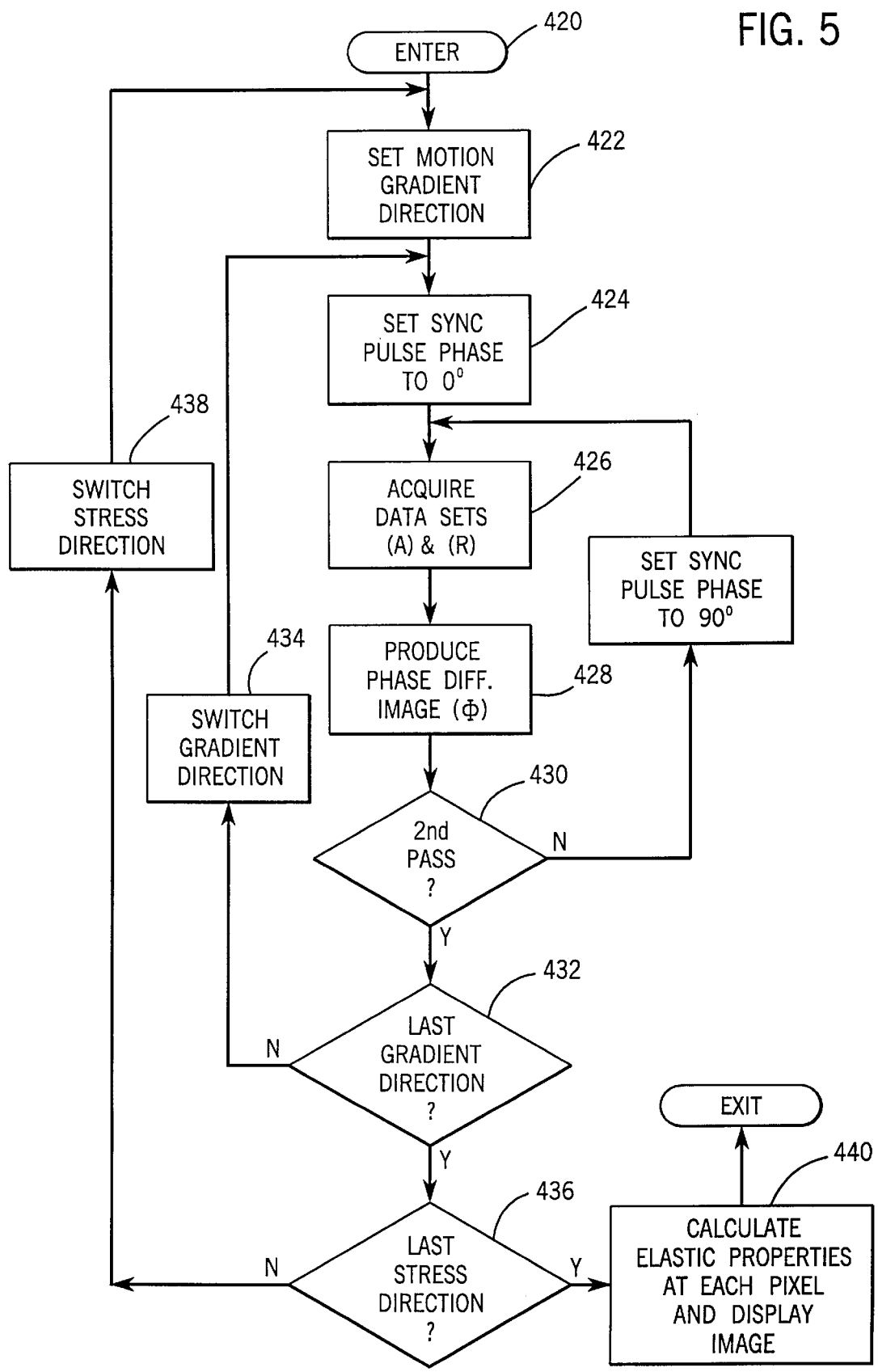
FIG. 5 is a flow chart which illustrates how the NMR system of FIG. 1 produces images indicative of the elastic properties in accordance with a second preferred embodiment of the invention using NMR data acquired with the pulse sequence of FIG. 3.

Referring particularly to FIG. 5, the scan begins at block 420 with the stress set to be applied along one axis. The direction of the alternating gradient is then set along the same axis at process block 422 and the phase of the sync pulses relative to the motion encoding gradient is set to zero as indicated at process block 424. The pulse sequence of FIG. 3 is then executed to acquire the two image data sets (A) and (R) at process block 426, as described above. A phase difference image (φ) is then produced as indicated at process block 428, and the system then loops back at decision block 430.

During the second pass, the sync pulse phase is offset 90° from the phase of the alternating gradient as indicated at process block 432, and another phase image (φ) is acquired and reconstructed. As a result, after two passes as detected at decision block 430, two phase images indicative of strain $S_L$ and $S_o$ are produced as defined above in respective equations (7) and (9). As discussed above, considerable information about the mechanical properties of the gyromagnetic media can be calculated from these two strain images alone.

However, the scan may proceed as indicated at decision block 432 to acquire further data from which more exhaustive mechanical properties can be measured. More specifically, the direction of the alternating gradient is changed to align along an orthogonal axis as indicated at process block 434, and two more strain images are acquired and reconstructed. This may be repeated again as determined at decision block 432 with the alternating gradient switched in direction to a third orthogonal axis at process block 434. Thus, two strain images $S_L$ and $S_o$ are produced with the alternating gradient directed along each of the three coordinate axes x, y and z to completely define the strain produced by the stress applied along one axis.

As indicated at decision block 436, the scan may continue by altering the direction of the applied stress. In most applications, this is accomplished by switching the sync pulses to a different stress transducer 130 that is oriented in an orthogonal direction to the first transducer 130, although it is also possible to pause the scan at this point and instruct the operator to change the location of the transducer 130. In any case, the direction of the applied oscillatory stress is switched as indicated at process block 438 and the system loops back to process block 422 to repeat the above-described measurements. This may be repeated again for a third orthogonal stress axis, as determined at decision block 436. If the scan is exhaustively executed, the following eighteen images are acquired and reconstructed:

| Image | STRESS AXIS | | | GRADIENT AXIS | | | SYNC PHASE | |
|---|---|---|---|---|---|---|---|---|
| | x | y | z | x | y | z | $S_L$ | $S_0$ |
| 1 | * | | | * | | | * | |
| 2 | * | | | * | | | | * |
| 3 | * | | | | * | | * | |
| 4 | * | | | | * | | | * |
| 5 | * | | | | | * | * | |
| 6 | * | | | | | * | | * |
| 7 | | * | | * | | | * | |
| 8 | | * | | * | | | | * |
| 9 | | * | | | * | | * | |
| 10 | | * | | | * | | | * |
| 11 | | * | | | | * | * | |
| 12 | | * | | | | * | | * |
| 13 | | | * | * | | | * | |
| 14 | | | * | * | | | | * |
| 15 | | | * | | * | | * | |
| 16 | | | * | | * | | | * |
| 17 | | | * | | | * | * | |
| 18 | | | * | | | * | | * |

It should be apparent that not all of these images need be acquired during a scan. Instead, the operator selects the elastic property or properties to be imaged and the program is configured to acquire and reconstruct the necessary strain images. From these strain images the desired elastic property can be calculated at each pixel, as indicated at process block 440 and described above under the heading "General Description of The Invention". The calculated values are then employed to modulate the intensity of its pixel location in an image.

Figure 6A:
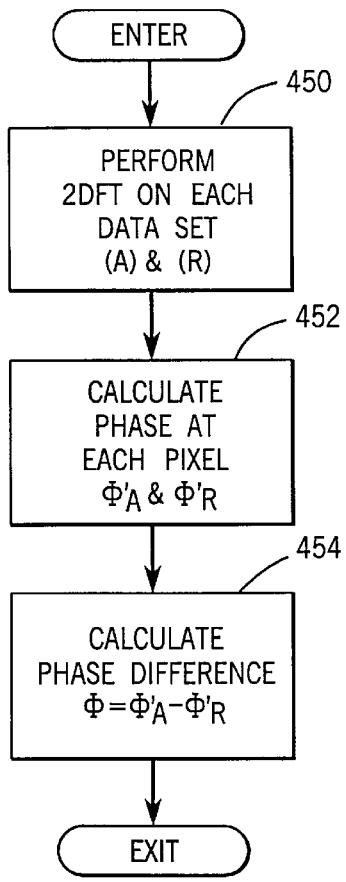
FIGS. 6a–c are flow charts of three different methods used to produce phase difference images in the methods of FIGS. 4 and 5.
Figure 6B:
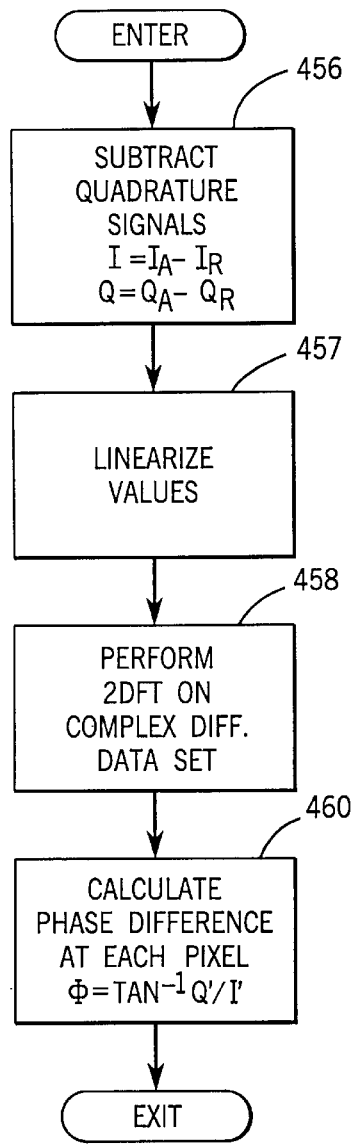
Figure 6C:
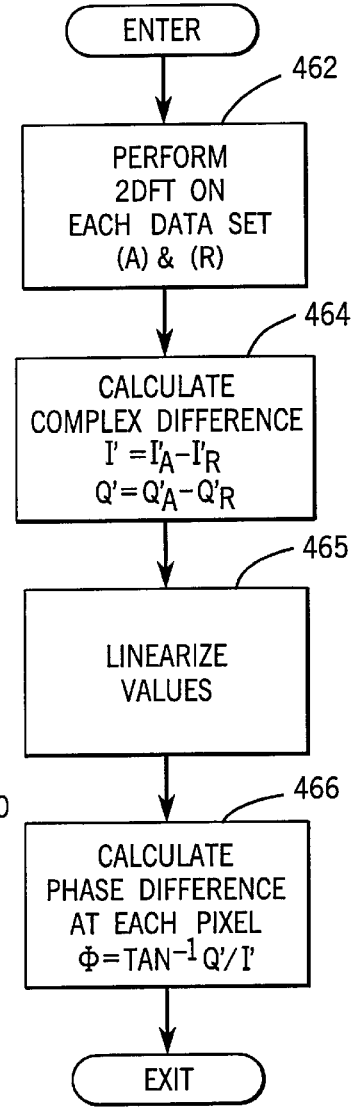

In the scans described above a phase image is produced from two acquired NMR data sets (A) and (R). Referring particularly to FIGS. 6A–C, there are three methods which may be used for performing this function. As shown in FIG. 6A at process block 450, in the first method a two-dimensional Fourier transformation ("2DFT") is performed on each acquired data set (A) and (R). The phase $\phi'_A$ is then calculated for each pixel location in the (A) image, and the phase $\phi'_R$ is calculated at each pixel of the (R) image as indicated at process block 452.

$$\phi'_A = \text{Tan}^{-1} Q'_A / I'_A$$

$$\phi'_R = \text{Tan}^{-1} Q'_R / I'_R$$

The phase difference ($\phi$) at each image pixel is then calculated at process block 454 by subtracting the reference phase $\phi'_R$ from the synchronous motion encoded phase $\phi'_A$.

The second method is referred to in the art as the complex difference technique. Referring particularly to FIG. 6B, the first step as indicated at process block 456 is to calculate the complex difference of the I and Q values of the corresponding sampled NMR signals in the two data sets (A) and (R). After these values are linearized, as indicated at process block 457, a two-dimensional Fourier transformation is performed on the resulting complex difference, as indicated at process block 458, and the phase $\phi$ at each pixel in the resulting image is calculated as indicated at process block 460.

The third method shown in FIG. 6C is very similar to the method of FIG. 6A. As indicated at process block 462, a two-dimensional Fourier transformation is performed on each NMR data set (A) and (R) and the complex difference between the resulting two images is calculated at process block 464. The resulting values are linearized as indicated at process block 465 and the phase of the resulting complex difference image is calculated at each pixel as indicated at process block 466.

It should be apparent to those skilled in the art that many variations are possible in the particular method used to acquire the NMR data and reconstruct an image indicative of the spin phase accumulated as a result of synchronous spin motion.

In the preferred embodiments described above, images are reconstructed in which pixel intensity is determined directly by the phase of the synchronous motion encoded NMR signals. Other, less direct methods for detecting the synchronous motion are also possible. For example, if the frequency of the synchronous motion and alternating magnetic field gradient is increased, the spatial wavelength of the strain waves in normal tissues approaches the dimension of an imaged voxel. As a result, significant NMR signal phase dispersion occurs within each voxel, and in a conventional image in which the brightness of each pixel is determined by the "modulus" (i.e. $\sqrt{I^2+Q^2}$) of the signal at each voxel, normal tissues will appear dark. On the other hand, the same strain waves passing through tumors and other less compliant tissues have a longer spatial wavelength and correspondingly less intravoxel phase dispersion. As a result, the signal intensity, or modulus, at these lesions will be much greater than the surrounding normal tissue and much brighter in the reconstructed image.

Another less direct method for detecting the synchronous spin motion is to encode the resulting phase accumulation in longitudinal magnetization by tipping the phase encoded transverse magnetization back to the longitudinal axis. A pulse sequence which uses this synchronous phase encoded longitudinal magnetization will produce a modulus image that depicts the strain wave pattern in the subject.

As indicated above, synchronous spin motion is produced using a transducer 130 that applies an oscillatory force to the gyromagnetic media. This force produces a corresponding stress in the gyromagnetic media which is propagated therethrough as strain in accordance with its elastic properties. This strain is the synchronous spin motion detected and imaged according to the present invention.

Figure 7A:
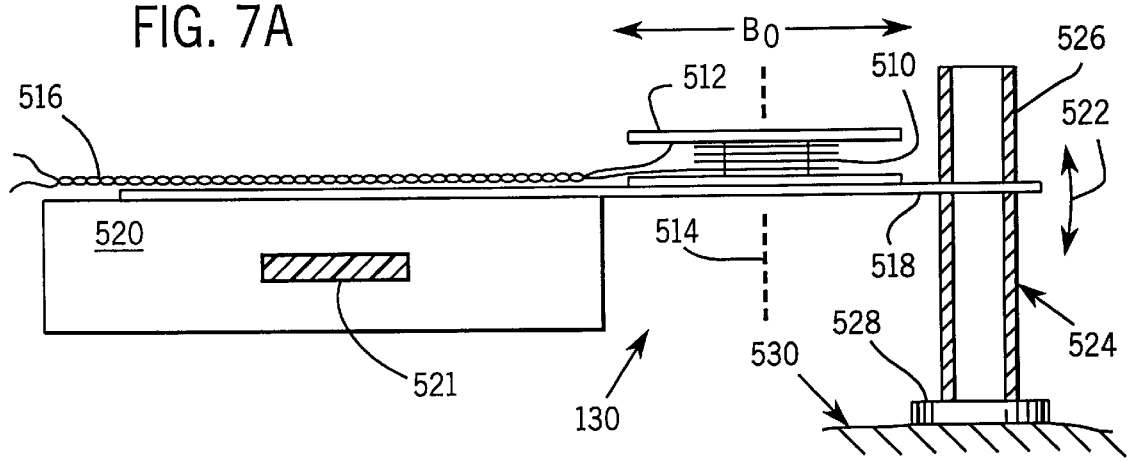
FIGS. 7a and 7b are elevation and top views respectively of a transducer that is used in the NMR system of FIG. 1 to practice the present invention.
Figure 7B:
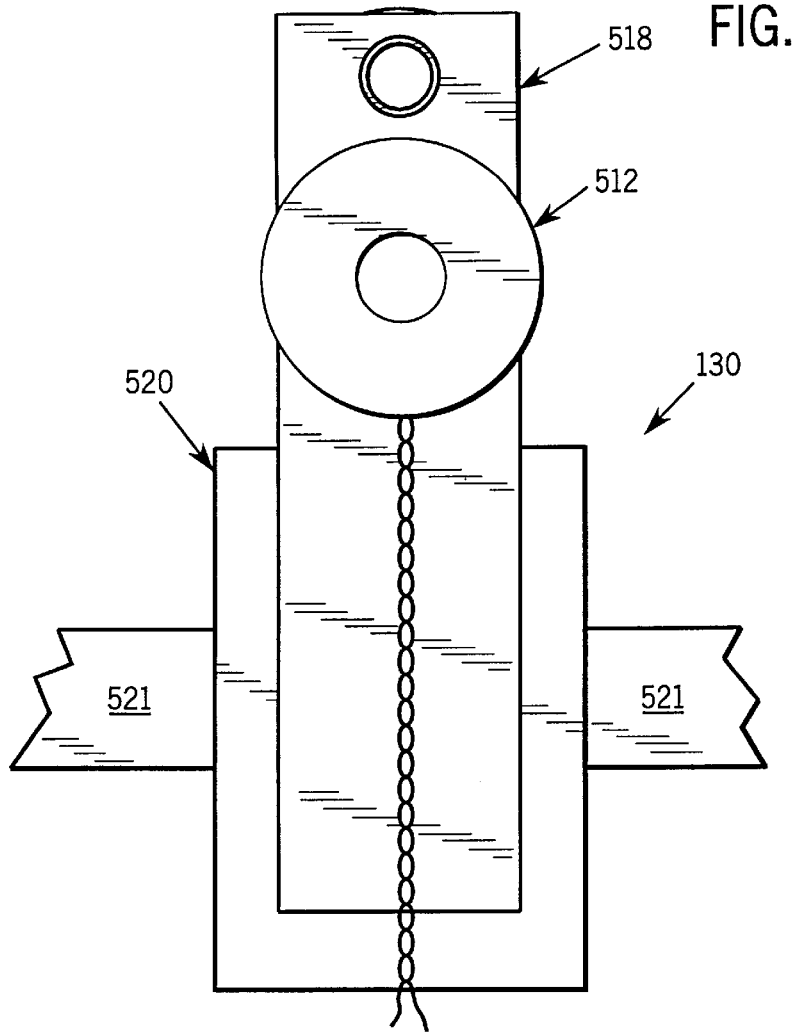

Referring particularly to FIGS. 7A and 7B, the preferred embodiment employs a transducer 130 suitable for applying an oscillatory force externally to a patient. It includes a coil of wire 510 wound on a bobbin 512, with the coil axis 514 directed perpendicular to the polarizing magnetic field $B_0$. The coil 510 is 400 turns of 30 AWG. copper wire, and its leads 516 are connected directly to the amplifier 129 as described above. The bobbin 512 is mounted to a flexible arm 518 that is attached to, and cantilevered from a supporting block 520. When a current passes through the coil 510, the magnetic field which it produces interacts with the polarizing field $B_o$. The bobbin 512 is thus twisted to bend the flexible arm 518 either upward or downward depending on the direction of current flow. By alternating the direction of current flow, the coil 510 twists back and forth to produce a corresponding alternating force which causes the flexible arm 518 to oscillate as indicated by the arrow 522. A strap 521 extends through an opening in the supporting block 520 and securely fastens it to the patient.

The oscillatory motion of the arm 518 is coupled to the subject 530 by an applicator 524. In its simplest form the applicator 524 is comprised of a tube 526 of the desired length which is secured at one of its ends to the arm 518. A pressure plate 528 is secured to the other end of the tube 526. The pressure plate 528 rests on the subject 530 to be imaged and its oscillatory movement produces a corresponding oscillatory compressive force that generates the desired synchronous spin motion.

Other applicators 524 may be used with the transducer 130 to couple the oscillatory motion of the flexible arm 518 to the subject. For example, the applicator 524 may take the form of a probe which is inserted into an opening in the subject to rest against a particular structure (such as the prostate gland), or it may be inserted through tissue and its end anchored to an internal structure (such as the liver). Many shapes and sizes are possible.

With the exception of the coil 510, all elements of the transducer 130 are constructed using non-magnetic materials. Thermoplastics such as acrylic may be used, for example, because such materials can be molded or machined into many desired shapes and they are relatively benign to the tissues which they contact.

For some applications it may be possible to produce the alternating gradient field pulses 315 with the same transducer 130 used to apply stress to the subject. In this case, the transducer 130 includes a coil that acts as a local gradient coil for surrounding tissues. The same alternating current applied to this coil to produce the alternating magnetic field gradient pulses 315 also cause the coil to move in an oscillatory manner at the same frequency and phase. Such a coil might be used, for example, to detect tumors in the prostate gland.

While application of a synchronous motion is preferably accomplished by the direct application of a force to the patient, indirect synchronous motion producing mechanisms are also possible. Electrical or other non-mechanical stimulation may be applied to the patient to produce synchronous motion in the tissues to be imaged. For example, synchronous brain function stimulation may produce synchronous motion at the cellular, or sub-cellular level. Synchronous electrical stimulation of selected muscles will, of course, produce synchronous motion in the muscles themselves, but also, detectable synchronous motion may be produced in the associated nerves and in tissues surrounding the muscles.

Rather than applying a separate synchronous stress or synchronous stimulation, an endogenous periodic motion may also be used to practice the present invention. In this case the alternating motion encoding magnetic field gradient must be synchronized with the endogenous motion, and for best results, this requires the detection of a signal indicative of the frequency and phase of the endogenous motion. For example, the rapid movement of an abnormal heart valve may be detected with a phonocardiogram that senses the sound produced by the valve. The resulting electrical signal is used to synchronize the alternating magnetic field gradient. The resulting synchronous motion of the valve itself, as well as surrounding tissues and the blood flowing through the valve may be imaged. Similar results may be achieved with the heart using the ECG signal.

Contrast agents are used in many imaging modalities to enhance image contrast in a diagnostically useful manner. Such a strategy is also possible with the present invention when the contrast agent operates to change the elastoviscous characteristics of the tissues of interest. For example, an osmotic agent which affects mechanical properties in a manner that may be detected using the present invention may be used. A hyper-osmolar agent will draw water out of the target cells and make them more compliant, whereas a hypo-osmolar agent will add water to the target cells and make them rigid, or less compliant. This compliance difference can be imaged with the present invention and thus the affected cells can be contrasted against other cells that do not respond to the contrast agent.

The present invention may also be used to enhance magnetic resonance angiograms ("MRA"). MRA relies on the movement of blood in the direction of one or more motion encoding magnetic field gradients to differentiate between stationary blood vessel walls and the blood which they carry. If the blood flow is slow, as in venous blood vessels, this contrast mechanism-is less effective. The present invention may be used to produce an MRA by applying a compressive force at the synchronous frequency which sends compression waves through the vasculature. Since blood is an incompressible liquid, the synchronous compression wave will travel quite efficiently through the vessels as an oscillatory motion of the blood cells at the synchronous frequency. The alternating magnetic field gradient is "tuned" to this synchronous frequency and the resulting phase image will depict the vasculature. An example of this application of the invention will now be described.

Figure 11:
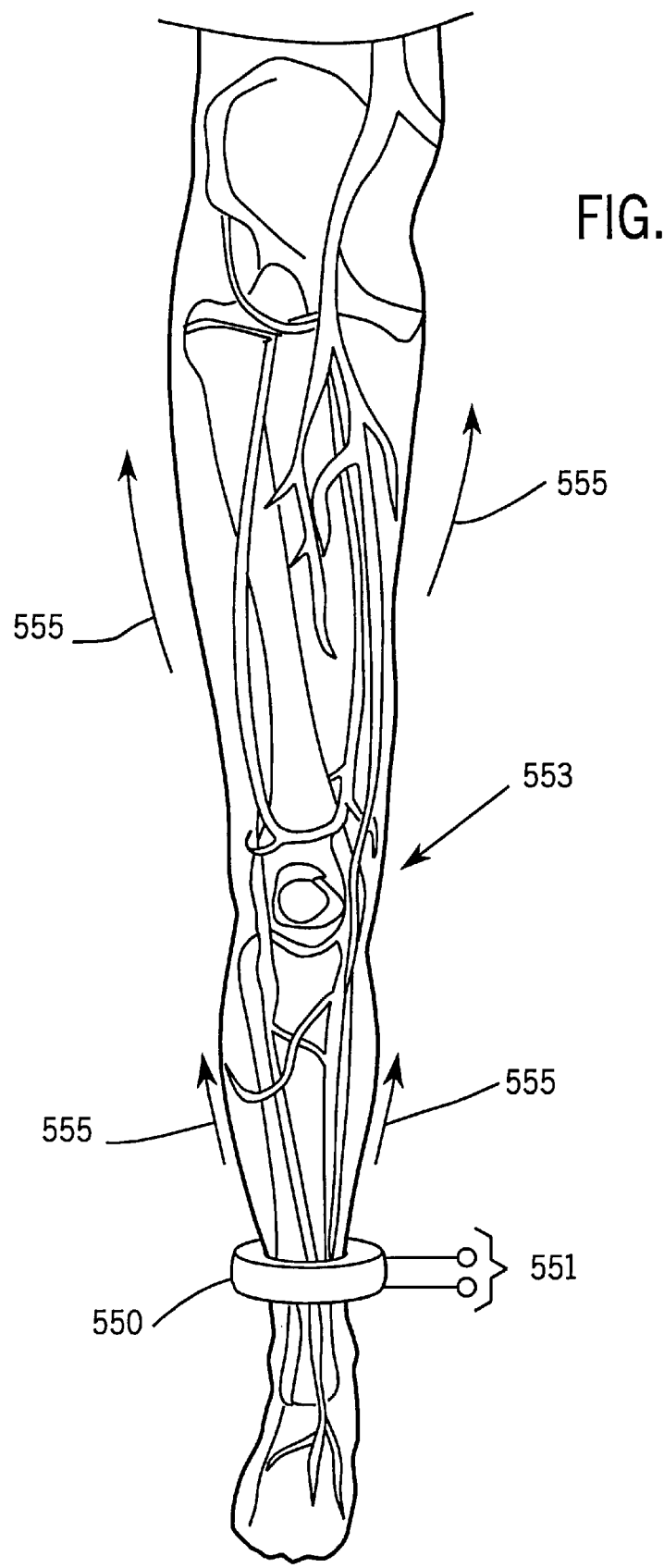
FIG. 11 is a pictorial representation of a human leg illustrating an alternative method for stimulating synchronous spin motion in blood vessels.

Referring particularly to FIG. 11, a cuff 550 is used in place of the transducer 130 in this embodiment of the invention. The cuff 550 receives the synchronous drive signal produced by the amplifier 129 (FIG. 1) at leads 551 and it constricts around the subject's ankle. The resulting synchronous compression waves in the venous structure and the arterial structure travel up the patient's leg 553 as indicated by arrows 555. The acquisition of a phase image as described above using the pulse sequence of FIG. 3 with a synchronous alternating magnetic field gradient 315 directed along the lengthwise dimension of the leg 553, may be used to produce an angiogram. To improve the SNR of the image additional phase images with the alternating magnetic field gradient directed along the other two orthogonal axes may also be acquired and summed together.

I claim:

1. A device for applying an oscillatory stress to a subject positioned in the polarizing magnetic field of an NMR imaging system, the combination comprising:

a supporting member positioned adjacent the subject and in the polarizing magnetic field;

a flexible arm fastened to the supporting member and extending outward therefrom;

a coil of conductive wire mounted to the flexible arm and having a pair of terminals for electrical connection to a current source; and an applicator connected to the flexible arm and shaped to mechanically couple motion of the flexible arm to the subject, and wherein the flexible arm is set in oscillatory motion by the application of an oscillating current to the coil terminals.

2. The device as recited in claim 1, in which the applicator is shaped to press against the surface of the subject.

3. The device as recited in claim 1, in which the applicator is shaped for insertion into an opening in the subject.

4. The device as recited in claim 1 in which the applicator is shaped for insertion into the subject.

* * * * *